United States Patent

Kondo et al.

Patent Number: 5,849,797
Date of Patent: Dec. 15, 1998

[54] D-β-LYSYLMETHANEDIAMINE DERIVATIVES AND PREPARATION THEREOF

[75] Inventors: Shinichi Kondo; Yoko Ikeda; Tomio Takeuchi; Rie Shinei; Shuichi Gomi; Seiji Shibahara, all of Tokyo; Hiroo Hoshino, Maebashi, all of Japan

[73] Assignee: Zaidan Hojin Biseibutsu Kagaku Kenkyu Kai, Japan

[21] Appl. No.: 793,912

[22] PCT Filed: Aug. 24, 1995

[86] PCT No.: PCT/JP95/01680

§ 371 Date: Feb. 24, 1997

§ 102(e) Date: Feb. 24, 1997

[87] PCT Pub. No.: WO96/06069

PCT Pub. Date: Feb. 29, 1996

[30] Foreign Application Priority Data

Aug. 24, 1994 [JP] Japan ................... 6-220830

[51] Int. Cl.$^6$ .................. A61K 31/16; C07C 231/02; C07C 233/05

[52] U.S. Cl. .................. 514/626; 514/138; 514/197; 514/198

[58] Field of Search .................. 564/197, 198, 564/138; 514/626

[56] References Cited

FOREIGN PATENT DOCUMENTS 9312776  7/1993  WIPO.

OTHER PUBLICATIONS

Ikeda et al, The Journal of Antibiotics, vol. 45, No. 10, 1677–1680, 1992.

Primary Examiner—Shailendra Kumar
Attorney, Agent, or Firm—Lalos & Keegan

[57] ABSTRACT

Now are provided (R)-3,6-diamino-N-(ω-aminoalkyl)-hexanamides which are novel compounds having the general formula (I):

$$H_2NCH_2CH_2CH_2\overset{(R)}{C}HCH_2CONH(CH_2)_nNH_2 \quad (I)$$
$$\underset{NH_2}{|}$$

wherein n stands for 2–5, and which may be for example, (R)-3,6-diamino-N-(2-aminoethyl)hexanamide (n=2) and (R)-3,6-diamino-N-(3-aminopropyl)hexanamide (n=3). Their preparation process is also provided. These novel compounds and acid addition salts thereof have activities inhibitory against Gram-positive bacteria, Gram-negative bacteria and AIDS virus, as well as tumor cells and are chemically stable.

These novel compounds and their salts are useful as chemotherapeutic agents for diseases caused by these bacteria or virus and also as antitumor agent.

8 Claims, No Drawings

D-β-LYSYLMETHANEDIAMINE DERIVATIVES AND PREPARATION THEREOF

This application is a 371 of PCT/JP95/01680, filed Aug. 24, 1995.

TECHNICAL FIELD

This invention relates to an (R)-3,6-diamino-N-(ω-aminoalkyl)hexanamide which is a novel compound active for inhibiting the growth of Gram-positive bacteria and Gram-negative bacteria, the infection of human T-cells with AIDS virus, namely HIV, and the growth of tumor cells and which is represented by the following general formula (I):

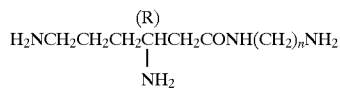

wherein n stands for an integer of 2–5. This novel compound of the general formula (I) above is useful as a chemotherapeutic agent for various purposes. This invention also relates to a process for the preparation of the above-described novel compound.

BACKGROUND ART

The present inventors discovered that D-β-lysyl-methanediamine which corresponds to such compound of the general formula (I) above where n stands for 1 and is hence represented by the formula (A):

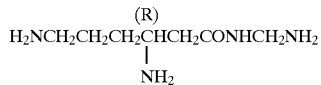

is produced and accumulated in a culture of an actinomycetes strain ("J. Antibiotics", 39, 476(1986) and Japanese Patent Application Laid-Open Publication No. SHO 62-114947, published May 26, 1987). Development and researches are now made for utilization of D-β-lysyl-methanediamine as a therapeutic agent for the treatment of AIDS (Japanese Patent Application No. HEI 3-346341 filed on Dec. 27, 1991; U.S. patent application Ser. No. 08/256,121; and European patent application publication No. 653207-A1).

AIDS is a disease caused by the infection with an AIDS virus (HIV). Several drugs which can inactivate HIV have been reported as therapeutics for AIDS, but any of them are not satisfactory. There is hence a continued demand for providing such a novel drug having low toxicity but high anti-HIV activities.

Through a study of the present inventors, the chemical structure of D-β-lysylmethanediamine (which is generally called "Bellenamine") was determined to be unique since its total synthesis was somewhat difficult with starting from an amino-protected D-β-lysylglycine via its acid azide ["J. Antibiotics", 45, 1677(1992)]. Owing to the high instability of D-β-lysylmethanediamine, its total synthesis process is troublesome to be achieved.

D-β-lysylmethanediamine, that is, Bellenamine, which was found in the culture of the microorganism of actinomycetes and discovered by the present inventors and which has anti-HIV activities, has the linear aldoaminal structure that is discovered firstly to exist in the nature, so that Bellenamine is chemically instable.

DISCLOSURE OF THE INVENTION

The present inventors therefore have now conducted research on the synthesis of novel and useful Bellenamine-related substances. An object of the present invention is to provide an (R)-3,6-diamino-N-(ω-aminoalkyl)hexanamide as a novel compound which can be considered to be analogous to D-β-lysylmethanediamine but is chemically more stable. Another objects of the present invention will be clear from the following descriptions.

The present inventors have now succeeded in synthesizing a series of (R)-3,6-diamino-N-(ω-aminoalkyl)hexanamides, which each is a novel compound having higher chemical stability than D-β-lysylmethanediamine and having antibacterial activity and anti-HIV activities as well as antitumor activity and which is collectively represented by the general formula (I) as above. It has now been found that among the compounds of the general formula (I), (R)-3,6-diamino-N-(2-aminoethyl)hexanamide and (R)-3,6-diamino-N-(3-aminopropyl)hexanamide have antibacterial and anti-HIV activities comparable to or sometime superior to those of D-β-lysylmethanediamine and also exhibit an antitumor activity superior to that of D-β-lysylmethanediamine.

According to a first aspect of the present invention, therefore, there is provided an (R)-3,6-diamino-N-(ω-aminoalkyl)hexanamide represented by the general formula (I):

wherein n stands for an integer of 2–5, or an acid addition salt thereof.

According to a second aspect of the present invention, there is provided a process for the preparation of an (R)-3,6-diamino-N-(ω-aminoalkyl)hexanamide represented by the general formula (I):

wherein n stands for an integer of 2–5, which comprises the steps of condensing, through an amido-bond, a mono-amino-protected derivative of an α,ω-alkanediamine represented by the general formula (II):

wherein A represents an aralkyloxycarbonyl group which is an amino-protecting group easily removable by hydrogenolysis and n stands for an integer of 2–5, with a bis(N-aralkyloxycarbonyl)-D-β-lysine represented by the general formula (III):

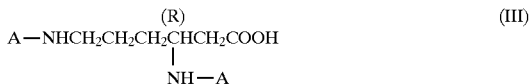

wherein A has the same meaning as described above, to form an (R)-3,6-bis(aralkyloxycarbonylamino)-N-(ω-aralkyloxycarbonylaminoalkyl)hexanamide represented by the general formula (IV):

wherein A and n have the same meanings as described above, and then subjecting the compound of the formula (IV) to hydrogenolysis to remove the aralkyloxycarbonyl groups therefrom.

The (R)-3,6-diamino-N-(ω-aminoalkyl)hexanamide of the general formula (I) synthesized as a novel compound according to the present invention or the acid addition salt thereof are chemically stable, and besides they have inhibitory activities against Gram-positive bacteria and Gram-negative bacteria and also against AIDS virus, as well as an antitumor activity against some kinds of tumor cells, so that they are useful as a chemotherapeutic agent for diseases caused by infection with these bacteria or virus and also are useful as an antitumor agent.

BEST MODE FOR CARRYING OUT THE INVENTION

A detailed description will hereinafter be made of the first aspect of the present invention.

When n stands for 2 in the compound of the general formula (I), there is provided (R)-3,6-diamino-N-(2-aminoethyl)hexanamide represented by the following formula (Ia):

When n stands for 3 in the compound of the general formula (I), there is provided (R)-3,6-diamino-N-(3-aminopropyl)hexanamide represented by the following formula (Ib):

Physicochemical properties of some examples of the novel compounds of the general formula (I) available according to the present invention will be described below.

[1] (R)-3,6-Diamino-N-(2-aminoethyl)hexanamide [the compound of the formula (Ia)]

(1) Color and appearance: a colorless paste
(2) Molecular formula: $C_8H_{20}N_4O$
(3) Mass spectrum (FD-MS): m/z 189 (MH⁺ High-resolution mass spectrum (HR-FAB-MS): m/z 189.1729 (MH⁺), Calculated for $C_8H_{21}N_4O$: 189.1715 (MH)
(4) Melting point: No definite melting point is observed.
(5) Specific optical rotation: $[\alpha]_D^{24}$–6.0° (c 1.2, $H_2O$)
(6) Infrared absorption spectrum (KBr): 3300, 2950, 1640, 1570, 1480, 1440, 1390, 1320, 1240, 1160, 1050, 820 $cm^{-1}$
(7) $^1$H-NMR spectrum (400 MHz, $D_2O$, pD4):
δ1.80(4 H, m, 4-$H_2$, 5-$H_2$)
2.67(1 H, dd, J=16.4, 8.5 Hz, 2-H)
2.80(1 H, dd, J=16.4, 4.6 Hz, 2-H)
3.07(2 H, m, 6-$H_2$)
3.18(2 H, t, J=5.9 Hz, 2'-$H_2$)
3.55(2 H, t, J=5.9 Hz, 1'-$H_2$)
3.71(1 H, m, 3-H)
(8) $^{13}$C-NMR spectrum (100 MHz, $D_2O$, pD 4):
δ23.8(t, C-5), 30.0(t, C-4), 37.3(t, C-2),
37.7(t, C-1'), 39.8(t, C-6), 40.0(t, C-2''),
49.1(d, C-3), 173.6(s, C-1)
(9) Solubility: highly soluble in water.
(10) Basic, acidic or neutral: basic substance.

[2] (R)-3,6-Diamino-N-(3-aminopropyl)hexanamide [the compound of the formula (Ib)]

(1) Color and appearance: a colorless paste
(2) Molecular formula: $C_9H_{22}N_4O$
(3) Mass spectrum (FD-MS): m/z 203 (MH⁺ High-resolution mass spectrum (HR-FAB-MS): m/z 203.1880 (MH⁺), Calculated for $C_9H_{23}N_4O$: 203.1872 (MH)
(4) Melting point: No definite melting point is observed.
(5) Specific optical rotation: $[\alpha]_D^{24}$–3.5°(c 0.9, $H_2O$)
(6) Infrared absorption spectrum (KBr): 3300, 2950, 1640, 1560, 1480, 1440, 1390, 1320, 1210, 1150, 1050, 820 $cm^1$
(7) $^1$H-NMR spectrum (400 MHz, $D_2O$, pD4):
δ1.79(4 H, m, 4-$H_2$, 5-$H_2$)
1.92(2 H, tt, J=7.3, 7.3Hz, 2'-$H_2$)
2.65(1 H, dd, J=16.4, 8.1Hz, 2-H)
2.76(1 H, dd, J=16.4, 5.1Hz, 2-H)
3.05(2H, t, J=7.3Hz, 3'-$H_2$)
3.07(2H, m, 6-$H_2$)
3.33(2H, m, 1'-$H_2$)
3.68(1 H, m, 3-H)
(8) $^{13}$C-NMR spectrum (100 MHz, $D_2O$, pD 4):
δ23.7(t, C-5), 27.4(t, C-2'), 29.9(t, C-4),
37.0(t, C-1'), 37.4(t, C-2), 37.9(t, C-3'),
39.7(t, C-6), 49.2(d, C-3), 172.8(s, C-1)
(9) Solubility: highly soluble in water.
(10) Basic, acidic or neutral: basic substance.

Each compound of the general formula (I) according to the present invention is strongly basic so that it can form an addition salt with an acid. Illustrative acids for the formation of acid addition salts may include pharmaceutically acceptable inorganic acids such as hydrochloric acid, sulfuric acid and carbonic acid; and pharmaceutically acceptable organic acids such as acetic acid, malic acid, citric acid, ascorbic acid and methanesulfonic acid.

Each compound of the general formula (I) according to the present invention or an acid addition salt thereof can be administered in the form of a preparation as mixed with a pharmaceutically acceptable solid or liquid carrier, and for example, may be given orally in the dosage form of powder, granules, tablets, syrup or the like, or parenterally in the dosage form of an injection or the like.

The biological properties of the novel (R)-3,6-diamino-N-(ω-aminoalkyl)hexanamide available according to the present invention are described below.

[1] Antibacterial activities

The minimum inhibitory concentrations (MIC.) of (R)-3, 6-diamino-N-(2-aminoethyl)hexanamide of the formula (Ia) and (R)-3,6-diamino-N-(3-aminopropyl)hexanamide of the formula (Ib) against the growth of various bacteria were determined by a serial dilution method on a 0.5% peptone agar medium (incubated at 37° C. for 18 hours). The results obtained are shown in Table 1 below, in comparison with the MIC. of D-β-lysylmethanediamine (Bellenamine).

TABLE 1

| Test Bacteria | MIC (μg/ml) | | |
| --- | --- | --- | --- |
| | Bellenamine (Comparative) | Invention compound (Ia) | Invention compound (Ib) |
| Staphylococcus aureus FDA209P | 50 | 25 | 200 |
| S. aureus Smith | 6.25 | 6.25 | 50 |
| Micrococcus luteus FDA16 | >200 | >200 | >200 |
| Bacillus anthracis | 100 | 100 | 200 |

TABLE 1-continued

| Test Bacteria | MIC (μg/ml) | | |
|---|---|---|---|
| | Bellenamine (Comparative) | Invention compound (Ia) | Invention compound (Ib) |
| B. subtilis NRRL B-558 | 12.5 | 25 | 100 |
| B. subtilis PC1219 | 12.5 | 25 | 100 |
| B. cereus ATCC10702 | 50 | 50 | 200 |
| Escherichia coli NIHJ | 200 | 100 | 200 |
| E. coli K-12 | >200 | 200 | 200 |
| Shigella dysenteriae JS11910 | >200 | 200 | 200 |
| S. flexnelli 4b JS1811 | >200 | 100 | 200 |
| Klebsiella pneumoniae PCI602 | >200 | 200 | >200 |
| Proteus vulgaris OX19 | >200 | 200 | 200 |
| P. mirabilis IFM OM-9 | 200 | 25 | 50 |
| Providencia rettgeri GN311 | 50 | 25 | 100 |
| P. rettgeri GN466 | 100 | 50 | 50 |
| Serratia marcescens | 200 | 100 | 200 |
| Pseudomonas aeruginosa A3 | 200 | 100 | 200 |

[2] Inhibitory activities against HIV infection In the following, there is described Test 1 which demonstrates the inhibitory activities of (R)-3,6-diamino-N-(2-aminoethyl) hexanamide (Ia) and (R)-3,6-diamino-N-(3-aminopropyl) hexanamide (Ib) against the infection of human T-cells with HIV, namely the AIDS virus.

Test 1

To a Costar 48-well plate, there were added 0.5 ml of a cell suspension of MT-4 cells, that is, a kind of the human T-cells (containing $1 \times 10^5$ cells/ml of a phosphate buffer) and 0.05 ml of a solution (in a phosphate buffer) containing a given amount of a tested compound per one well. After incubation for 2 hours at 37° C. in an incubator under 5% $CO_2$, the MT-4 cells were infected with 0.05 ml of a suspension of HIV (HTLV-III$_B$ strain) in an amount of multiplicity of infection (m.o.i) of 0.025–0.05, followed by further incubation for 4 days.

Portions of the incubated cultures were taken and the MT-4 cells were smeared onto slide glasses, dried and immobilized with acetone. The presence of the HIV antigen-positive MT-4 cells was detected by the indirect immunofluorescent antibody assay method [Y. Hinuma et al., "Proc. Natl. Acad. Sci. USA," 78, 6476–6480, (1981) and Y. Takeuchi et al., "Gann.", 78, 11–15 (1987)]. To this end, the cell smears, that is, the acetone-immobilized cell smears were treated at 37° C. for 30 minutes with such serum of AIDS patient at a dilution of 1:10 in phosphate buffered saline, which was employed as the first antibody. After washing subsequently with phosphate buffered saline, the MT-4 cells were treated at 37° C. for 30 minutes with fluorescent isothiocyanate-conjugated rabbit anti-human IgG serum (Cappel Laboratories, Cocharanville, Pa., USA), which was employed as the second antibody. After the cell smears were then washed with phosphate buffered saline and covered with a cover glass, the MT-4 cells were examined under a fluorescence microscope. Percentages of the number of the viral antigen-positive MT-4 cells (namely, immunofluorescent cells where the HIV-associated antigens were present and expressed) in total cells were calculated.

For the control tests of estimating the number of the total cells under test, the above test procedures were repeated without addition of the tested compound.

Furthermore, cytotoxicity of the tested compound to the MT-4 cells was estimated. This was done by incubating the MT-4 cells at varying concentrations of the tested compound and in the absence of HIV but in the same manner of incubation and under the same conditions of incubation of MT-4 cells as those employed in the above-mentioned test procedures of assaying the activity of the tested compound to inhibit the infection of T-cells with HIV. That the cytotoxicity was not observed is represented by the symbol "–" in Table 2 below.

In order to evaluate the activity of the tested compound (Ia) or (Ib) to inhibit the infection of the MT-4 cells with HIV, calculation was made of the percentages (T/C, %) of the number (T) of the HIV antigen-positive cells as measured in the above-mentioned tests where the incubation of MT-4 cells was effected in the presence of the tested compound, against the number (C) of the HIV antigen-positive cells as measured in the above-mentioned control tests where the incubation of MT-4 cells was effected without the addition of the tested compound. The results of such calculation of the T/C values (%) are shown in Table 2 below, in term of rate (%) of presence or occurrence of the HIV antigen-positive cells.

TABLE 2

| Concentration of test compound (μg/ml) | Rate (%) of presence of HIV antigen-positive cells, and Cytotoxicity (given in brackets) | | |
|---|---|---|---|
| | Bellenamine (Comparative) | Invention compound (Ia) | Invention compound (Ib) |
| 0 | 90 | 90 | 90 |
| | (–) | (–) | (–) |
| 0.1 | 50 | 90 | 80 |
| | (–) | (–) | (–) |
| 1 | 5 | 80 | 10 |
| | (–) | (–) | (–) |
| 10 | 10 | 30 | 5 |
| | (–) | (–) | (–) |

As is apparent from the test results shown in Table 2, it is shown that (R)-3,6-diamino-N-(2-aminoethyl) hexanamide (Ia) and (R)-3,6-diamino-N-(3-aminopropyl) hexanamide (Ib) according to the present invention have anti-HIV activities comparable to or sometime superior to those of D-β-lysylmethanediamine (Bellenamine) as a comparative drug, and they do not have cytotoxicity.

This indicates that the addition and co-existence of an (R)-3,6-diamino-N-(ω-aminoalkyl)hexanamide according to this invention does not allow HIV to proliferate in human MT-4 cells but can inhibit development of HIV antigen in the MT-4 cells. The novel compounds of the formula (I) according to this invention have therefore been confirmed to exhibit strong inhibitory activities agsint the infection of human T-cells with HIV.

[3] Acute Toxicity

In tests for estimation of acute toxicity by intravenous injection to mice, the novel compounds of the formula (I) according to this invention, particularly (R)-3,6-diamino-N-(2-aminoethyl)hexanamide (Ia) and (R)-3,6-diamino-N-(3-aminopropyl)hexanamide (Ib) did not cause death of mice at a dosage of 250 mg/kg. As a result, these compounds are therefore proved to have a low toxicity.

[4] Antitumor Activity

The (R)-3,6-diamino-N-(ω-aminoalkyl)hexanamide of the general formula (I) according to this invention can further exhibit an antitumor activity against the growth of tumor cells. To demonstrate this, mouse leukemia P388 cells as representative tumor cells were incubated in a culture medium in the presence of (R)-3,6-diamino-N-(2-aminoethyl)hexanamide (Ia) or (R)-3,6-diamino-N-(3-aminopropyl)hexanamide (Ib) as added at different concentrations of the tested compound. In this way, such concentration of the tested compound which can inhibit the growth of the P388 cells by 50%, that is, the IC$_{50}$-value of the tested compound against the P388 cells was estimated. For comparison purpose, Bellenamine was tested in the same manner as above. The test results obtained are summarized in Table 3 below.

TABLE 3

| Tested Compound | IC$_{50}$-value (µg/ml) |
| --- | --- |
| Invention Compound (Ia) | 0.012 |
| Invention Compound (Ib) | 0.028 |
| Bellenamine (comparative) | 0.36 |

From the results of Table 3, it is shown that the tested compound of this invention can exhibit a higher antitumor activity than Bellenamine against the mouse leukemia P388 tumor cells.

Next, the production of the novel compound of the general formula (I) according to the present invention will be described in details.

In the process for the preparation of the novel compound of the general formula (I) according to the aforesaid second aspect of this invention, there is employed as the starting compound such a mono-amino-protected derivative of the α,ω-alkanediamine as represented by the general formula (II) shown hereinbefore. This mono-amino-protected derivative of the formula (II) may be prepared by anyone of known various methods but preferably may be prepared in accordance with the method of Atwell & Denny [see the "Synthesis", page 1032 (1984)]. More specifically, for example, an aqueous solution of propane-1,3-diamine is adjusted to pH 3.8 with methane-sulfonic acid, followed by addition of ethanol. The resulting solution is added dropwise with a solution of benzyloxycarbonyl chloride in dimethoxyethane under stirring at 20° C. At the same time, to the resulting mixture is added an aqueous solution of potassium acetate so that the pH of the reaction mixture is maintained at 3.5–4.5 during the reaction, whereby one of the amino groups of the propane-1,3-diamine can be selectively benzyloxycarbonylated to afford N-(benzyloxycarbonyl)-propane-1,3-diamine in a high yield (see Referential Example 2 given hereinafter).

The bis(N-aralkyloxycarbonyl)-D-β-lysine of the formula (III) to be used as the reactant may be bis(N-benzyloxycarbonyl)-D-β-lysine (see Referential Example 3 given hereinafter) which is available by the method of the present inventors [see "J. Antibiotics", 45, 1677(1992)].

In the process of the second aspect of the present invention, the reaction for condensation of the compound of the formula (II) with the compound of the formula (III) via the amido-bond can be conducted by using a known method such as the active ester method, the acid halide method or the like.

As the amino-protecting groups for use in the process of the second aspect of the invention, there can be employed various known amino-protecting groups, including alkyloxycarbonyl groups. It is however desirable to select such amino-protecting groups which can readily be removed under mild reaction conditions enough to avoid any further change to occur in the reaction product as formed. Preferred examples of the amino-protecting group include aralkyloxycarbonyl groups, such as benzyloxycarbonyl, para-methoxybenzyloxycarbonyl and the like, which can be eliminated easily by hydrogenolysis.

An (R)-3,6-diamino-N-(ω-aminoalkyl)hexanamide of the general formula (I) according to the present invention or a pharmaceutically acceptable salt thereof may be admixed with a pharmaceutically acceptable solid or liquid carrier so as to form a pharmaceutical composition comprising the compound of the formula (I) or the salt thereof as the active ingredient, which may be administered orally or parenterally.

According to a third aspect of the present invention, therefore, there is provided a pharmaceutical composition, which comprises as active ingredient an (R)-3,6-diamino-N-(ω-aminoalkyl)hexanamide represented by the general formula (I):

wherein n stands for an integer of 2–5, or an acid addition salt thereof, in association with a pharmaceutically acceptable carrier for the active ingredient.

The pharmaceutical composition according to the third aspect of the present invention may be prepared in the form of various formulations such as injections, oral preparations, suppositories or the like containing the active compound of the formula (I) or a salt thereof as mixed with a pharmaceutically acceptable carrier or excipient. Any pharmaceutically acceptable carrier or excipient are selectable for that purpose. The nature and composition of the carrier used may vary depending on the administration route and manner. For example, water, ethanol, an animal or vegetable oil such as soybean oil, sesame oil or mineral oil, or a synthetic oil may be used as a liquid carrier. Usable solid carriers include, for example, a sugar such as maltose or sucrose, an amino acid such as lysine, a cellulose derivative such as hydroxypropylcellulose, a polysaccharide such as cyclodextrin, a salt of an organic acid such as magnesium stearate, or the like.

For the injections being prepared, it is generally preferable that the liquid medium of the injections comprises physiological saline, various buffered solutions, an aqueous solution of a sugar such as glucose, inositol or mannitol, or a glycol such as ethylene glycol or polyethylene glycol. It is also feasible to formulate a lyophilized preparation containing the compound of the formula (I) or a salt thereof as the active ingredient in association with an excipient, e.g., a sugar such as inositol, mannitol, glucose, mannose, maltose or sucrose or an amino acid such as phenylalanine. Upon administration, such lyophilized preparation may be dissolved in a suitable solvent for injection, for example, sterilized water or an intravenously-administrable liquid such as physiological saline, aqueous solution of glucose, an aqueous solution of electrolytes or an aqueous solution of amino acids.

Although the proportion of the compound of the formula (I) present in the formulated composition may widely vary from one preparation to another preparations, it may generally be in a range of 0.1–95 % by weight, preferably 1–90 % by weight. Upon the preparation of an injection, for example, it is generally desirable that the injectionable solution contains the compound of the formula (I) as active ingredient at a concentration of 0.1–5 % by weight. For oral administration, the compound (I) as the active ingredient may be formulated into tablets, capsules, a powder, granules in combination with the solid carrier or may be formulated into a solution, a dry syrup or the like in combination with the liquid carrier. In capsules, tablets, granules or a powder, the proportion of the compound of the formula (I) as the active ingredient present therein may usually be in a range of about 3–95 wt.%, preferably 5–90 wt.%, with the balance being formed of a carrier.

The dosage of the compound of the formula (I) may suitably be determined in account of the age, body weight, symptom of patients and therapeutic purpose as intended. The therapeutic, i.e., effective dosage of the compound of the formula (I) may be generally in a range of 1–100 mg/kg/day for the parenteral administration and in a range of 5–500 mg/kg/day for the oral administration. This dosage can be administered either continuously or intermittently as long as the total dosage does not exceed such a spcific level that was decided in view of results of animal tests and various circumstances.

Similarly, the total dosage of the compound of the formula (I) given by the parenteral administration may vary suitably depending on the way of administration, conditions of the patient or animal under treatment, for example, the age, body weight, sex, sensitivity, foods or feed, administration time, administration route, drugs adminstered concurrently, conditions of the patient and disease. The suitable dosage and administration frequency of the compound of the formula (I) under given conditions must be determined by an expert physician through the tests of determining optimal dosage and in light of the above guidelines. These requirements for administration should also apply to the oral administration of the compound of the formula (I).

In a further aspect, the present invention embraces use of an (R)-3,6-diamino-N-(ω-aminoalkyl)hexanamide of the general formula (I) as defined hereinbefore or a pharmaceutically acceptable salt thereof, in the manufacture of a pharmaceutical composition for inhibiting infection of human T-cells with AIDS virus.

In another aspect, the present invention includes use of an (R)-3,6-diamino-N-(ω-aminoalkyl)hexanamide of the general formula (I) as defined above or a pharmaceutically acceptable salt thereof, in the manufacture of an antibacterial composition.

In a still another aspect, the present invention includes use of an (R)-3,6-diamino-N-(ω-aminoalkyl)-hexanamide of the general formula (I) as defined above or a pharmaceutically acceptable salt thereof, in the manufacture of an antitumor composition.

The present invention will hereinafter be illustrated with reference to the following Referential Examples and Examples. It should however be noticed that this invention is in no way limited to or by the Examples.

REFERENTIAL EXAMPLE 1

Preparation of N-(benzyloxycarbonyl)ethylenediamine
This preparation was conducted in accordance with the method proposed by Atwell et al. ["Synthesis", pp. 1032–1033(1984)]

In 7 ml of water were dissolved 2.4 ml (35.9 mmol) of ethylenediamine. An aqueous solution (7 ml) of methanesulfonic acid (4.3 ml, 66.3 mmol) was added to the resulting solution to adjust its pH to 3.7. The aqueous solution obtained was diluted with 20 ml of ethanol, followed by dropwise addition thereto of a solution (7 ml) of benzyl chloroformate (4.5 ml, 31.5 mmol) in dimethoxy-ethane under vigorous stirring at 20° C. At the same time, a 50%(w/v) aqueous solution of potassium acetate was added dropwise to the resulting reaction mixture so that the pH of the reaction mixture was maintained at 3.5–4.5. After the addition of benzyl chloroformate, the resulting mixture was stirred for one hour at room temperature. The reaction solution so obtained was then concentrated to dryness.

To the residue so obtained were added 70 ml of water. The resulting mixture was stirred and then, an insoluble matter was filtered off therefrom. The filtrate was washed thrice with benzene (20 ml), adjusted to pH 10 or more with a 10N aqueous solution of sodium hydroxide and then extracted twice with benzene (40 ml). The benzene layer (the extracts) obtained was washed with 40 ml of a saturated aqueous solution of sodium chloride, dried over anhydrous sodium sulfate and concentrated to dryness, whereby 4.30 g of a crude product of the above-titled compound were obtained. This crude product obtained was loaded on an upper part of a silica gel column (430 g, "C-300"; trade name, a product of Wako Purechemical Industries, Ltd.) which had been packed with a 5:1 mixed solvent of chloroform and methanol in advance, and the column was then developed using the same mixed solvent as a developer. Fractions of the eluate which showed a ninhydrin-positive single spot on TLC were combined together and concentrated to dryness. Thus, 3.90 g of N-(benzyloxycarbonyl)ethylenediamine were afforded as a colorless paste.

REFERENTIAL EXAMPLE 2

Preparation of N-(benzyloxycarbonyl)propane-1,3-diamine
This preparation was conducted again in accordance with the method proposed by Atwell et al. ["Synthesis", pp. 1032–1033(1984)]

In 7 ml of water were dissolved 3.0 ml (35.9 mmol) of propane-1,3-diamine. An aqueous solution (7 ml) of methanesulfonic acid (4.3 ml, 66.3 mmol) was added to the resulting solution to adjust its pH to 3.8. The aqueous solution obtained was diluted with 19.5 ml of ethanol, followed by dropwise addition of a solution (7 ml) of benzyl chloroformate (4.5 ml, 31.5 mmol) in dimethoxyethane under vigorous stirring at 20° C. At the same time, a 50%(w/v) aqueous solution of potassium acetate was added dropwise to the resulting reaction mixture so that the pH of the reaction mixture was maintained at 3.5–4.5. After the addition of benzyl chloroformate, the resulting mixture was stirred for one hour at room temperature. The reaction solution so obtained was then concentrated to dryness.

To the residue obtained were added 70 ml of water. After the resulting mixture was stirred, an insoluble matter was filtered off therefrom. The filtrate was washed thrice with benzene (21 ml), adjusted to pH 10 or more with a 10N aqueous solution of sodium hydroxide and then extracted twice with benzene (40 ml). The benzene layer (the extracts) obtained was washed with 40 ml of a saturated aqueous solution of sodium chloride, dried over anhydrous sodium sulfate and concentrated to dryness, whereby 3.34 g of a crude product of the above titled compound were obtained. This crude product obtained was loaded on an upper part of a silica gel column (330 g, "C-300"; trade name, a product of Wako Purechemical Industries, Ltd.) which had been packed with a 5:1 mixed solvent of chloroform and methanol in advance, and the column was then developed using the same mixed solvent as a developer. Fractions of the eluate which showed a ninhydrin-positive single spot on TLC were combined together and concentrated to dryness. Thus, 2.95 g of N-(benzyloxycarbonyl)propane-1,3-diamine were afforded as a colorless paste.

REFERENTIAL EXAMPLE 3

Preparation of bis(N-benzyloxycarbonyl)-D-β-lysine
In 50 % aqueous methanol were dissolved 68.7 mg (0.47 mmol) of D-β-lysine, and the resulting solution was added with 399.5 mg (1.46 mmol) of benzyl S-4,6-dimethyl-pyrimid-2-ylthiocarbonate (product of Kokusan Chemical Works, Ltd.) and 0.135 ml (0.96 mmol) of triethylamine. The resulting mixture was stirred overnight at room temperature. The reaction solution obtained was concentrated to dryness, followed by washing the residue with aqueous methanol, to give 150mg of (N-benzyloxycarbonyl)-D-β-lysine as colorless powder (yield: 77%).

EXAMPLE 1

Preparation of (R)-3,6-bis(benzyloxycarbonylamino)-N-(2-benzyloxycarbonylaminoethyl)hexanamide (corresponding to the compound of the formula (IV) where A represents a benzyloxycarbonyl group and n stands for 2)

In 12 ml of dioxane were dissolved 401 mg (0.968 mmol) of bis(N-benzyloxycarbonyl)-D-β-lysine, and the resultant solution was then added with 124 mg (1.077 mmol) of N-hydroxysuccinimide and 225 mg (1.090 mmol) of dicyclo-hexylcarbodiimide. The resulting mixture was stirred at room temperature for 21 hours, and the precipitate as formed was then filtered off therefrom. To the resulting filtrate, there were added a suspension (6 ml) of N-(benzyloxycarbonyl)ethylenediamine (284 mg, 1,460 mmol) in dioxane and an aqueous solution (10 ml) of 125 mg (1.488 mmol) of sodium hydrogen carbonate, followed by stirring the resulting mixture at room temperature for 3 hours.

The precipitate as produced was collected by filtration. The precipitate was washed successively with 5 ml of water and 5 ml of cold dioxane and then dried to yield 565 mg of a crude powder. The crude powder obtained was loaded on an upper part of a silica gel column (56 g, "C-300"; trade name, a product of Wako Purechemical Industries, Ltd.), which had been packed with a 20:1 mixed solvent of chloroform and methanol in advance, and the column was then subjected to development using the same mixed solvent as a developer. Fractions of the eluate which showed a ninhydrin-positive single spot on TLC were combined together and concentrated to dryness. In this way, 530 mg of the titled compound were obtained as a colorless powder.

SI-MS: m/z 591 (MH$^+$), [α]$_D^{24}$+3.2°(c 1.08, DMSO)

EXAMPLE 2

Preparation of (R)-3,6-diamino-N-(2-aminoethyl)-hexanamide of the formula (Ia):

In 180 ml of methanol were suspended 1.41 g (2.39 mmol) of (R)-3,6-bis(benzyloxycarbonylamino)-N-(2-benzyloxycarbonylaminoethyl)hexanamide. To the resulting suspension was added a suspension of 718 mg of 10% palladium-carbon in 20 ml of water. After stirring, hydrogen gas was passed through the resulting mixture at room temperature for 3 hours to effect the reaction. The palladium-corbon was filtered off from the reaction mixture obtained, and the filtrate was concentrated to dryness. The residue obtained was dissolved in 15 ml of water and then subjected to a chromatography on a column of "Amberlite CG-50" (trade name, NH$_4^+$-form, 50 ml). After the column was washed with 200 ml of water, the column was eluted with aqueous ammonia at concentrations gradiently varying from 0.5% to 4.0% (0.5%-increased steps; 200 ml at each concentration). Fractions of the eluate as eluted with 2.5% to 3.5% aqueous ammonia were combined together and concentrated to dryness, to afford 445 mg of (R)-3,6-diamino-N-(2-aminoethyl)hexanamide as a colorless paste.

EXAMPLE 3

Preparation of (R)-3,6-bis(benzyloxycarbonylamino)-N-(3-benzyloxycarbonylaminopropyl)hexanamide (corresponding to the compound of the formula (IV) where A represents a benzyloxycarbonyl group and n stands for 3)

In 4 ml of dioxane were dissolved 195 mg (0.926 mmol) of bis(N-benzyloxycarbonyl)-D-β-lysine were dissolved, and the resulting solution was added with 43.0 mg (0.374 mmol) of N-hydroxysuccinimide and 74.0 g (0.359 mmol) of dicyclohexylcarbodiimide. The resulting mixture was stirred at room temperature for 18 hours, and precipitate as formed was filtered off therefrom. The resulting filtrate was added with a suspension (2 ml) of N-(benzyloxycarbonyl)propane-1,3-diamine (103 mg, 0.495 mmol) in dioxane and an aqueous solution (3.5 ml) of sodium hydrogen carbonate (44 mg, 0,524 mmol), followed by stirring the resultant mixture at room temperature for 4 hours. The reaction solution so obtained was then added with 40 ml of water, followed by extracting twice with 50 ml of chloroform. The chloroform layer (the extracts) was dried over anhydrous sodium sulfate and then concentrated to dryness, to give 217 mg of a crude powder. This crude powder obtained was purified by preparative TLC ("Art. No. 5744"; trade name, product of Merck A.G., Germany) with using a 20:1 mixed solvent of chloroform and methanol as the eluent. Thus, 183 mg of the titled compound were obtained as colorless powder.

SI-MS: m/z 605(MH$^+$), [α]$_D^{24}$+1.3° (c 1.06, DMSO)

EXAMPLE 4

Preparation of (R)-3,6-diamino-N-(3-aminopropyl)-hexanamide of the formula (Ib)

In 18 ml of methanol were suspended 144 mg (0.238 mmol) of (R)-3,6-bis(benzyloxycarbonylamino)-N-(3-benzyloxycarbonylaminopropyl)hexanamide. To the resulting suspension was added a suspension of 81.0 mg of 10% palladium-carbon in 2 ml of water, followed by stirring. Hydrogen gas was passed through the resulting mixture at room temperature for 3 hours to effect the hydrogenolysis reaction. The palladium-carbon was filtered off from the reaction mixture obtained, and the filtrate was then concentrated to dryness. The residue obtained was dissolved in 1 ml of water and the resulting solution was subjected to chromatography on a column of "Amberlite CG-50" (trade name, NH$_4^+$-form, 5 ml). After the column was washed with 25 ml of water, the column was eluted with aqueous ammonia at concentrations gradiently varying from 0.5% to 7.0% (0.5%-increased steps; 25 ml at each concentration). Fractions of the eluate as eluted with 4.0% to 6.0% aqueous ammonia were combined together and concentrated to dryness, to afford 48.2 mg of (R)-3,6-diamino-N-(3-aminopropyl)hexanamide as a colorless paste.

INDUSTRIAL APPLICAPABILITY OF INVENTION

The new compounds, (R)-3,6-diamino-N-(ω-aminoalkyl) hexanamide of the general formula (I) are now synthesized in accordance with the present invention, as described hereinbefore. These new compounds and their acid addition salts are chemically stable and have an activity of inhibiting the growth of Gram-positive bacteria and Gram-negative bacteria and also an activity of inhibiting the infection of human T-cells with AIDS virus, as well as an activity of inhibiting the growth of tumor cells, so that these new compounds are useful as a chemotherapeutic agent for treatment of bacterial infections and HIV infection, and also as an antitumor agent.

We claim:

1. An (R)-3,6-diamino-N-(ω-aminoalkyl)hexanamide represented by the general formula (I):

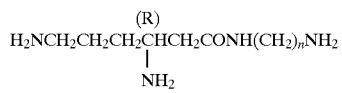
(I)

wherein n stands for an integer of 2 or 3 and (R) means (R)-configuration, or an acid addition salt thereof.

2. A compound according to claim 1 wherein n stands for 2 in the general formula (I), which is (R)-3,6-diamino-N-(2-aminoethyl)hexanamide, or an acid addition salt thereof.

3. A compound according to claim 1 wherein n stands for 3 in the general formula (I), which is (R)-3,6-diamino-N-(3-aminopropyl)hexanamide, or an acid addition salt hereof.

4. A process for the preparation of an (R)-3,6-diamino-N-(ω-aminoalkyl)hexanamide represented by the general formula (I):

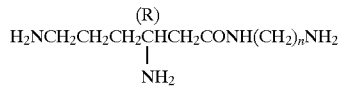
(I)

wherein n stands for an integer of 2 or 3 and (R) means (R)-configuration, which comprises the steps of condensing, through an amido-bond, a mono-amino-protected derivative of an α,ω-alkanediamine represented by the general formula (II):

(II)

wherein A represents an aralkyloxycarbonyl group which is an amino-protecting group easily removable by hydrogenolysis and n stands for an integer of 2 or 3, with a bis(N-aralkyloxycarbonyl)-D-β-lysine represented by the general formula (III):

(III)

wherein A has the same meaning as described above, to form an (R)-3,6-bis(aralkyloxycarbonylamino)-N-(ω-aralkyloxycarbonylaminoalkyl)hexanamide represented by the following general formula (IV):

(IV)

wherein A and n have the same meanings as described above, and then subjecting the compound of the formula (IV) to hydrogenolysis to remove the amino-protecting aralkyloxycarbonyl groups therefrom.

5. A pharmaceutical composition, which comprises as active ingredient an (R) -3,6-diamino-N-(ω-aminoalkyl)-hexanamide represented by the general formula (I):

(I)

wherein n stands for an integer of 2 or 3 and (R) means (R)-configuration, or an acid addition salt thereof, in association with a pharmaceutically acceptable carrier for the active ingredient.

6. The method of treating infection of a subject with AIDS virus comprising: treating said subject with an (R)-3,6-diamino-N-(ω-aminoalkyl)-hexanamide of the general formula (I) as defined in claim 1 or a pharmaceutically acceptable salt thereof.

7. The method of inhibiting the growth of bacteria comprising, treating said bacteria with an (R)-3,6-diamino-N-(ω-aminoalkyl)-hexanamide of the general formula (I) as defined in claim 1 or a pharmaceutically acceptable salt thereof.

8. The method of treating tumor growth comprising, treating said tumor with an (R)-3,6-diamino-N-(ω-aminoalkyl)-hexanamide of the general formula (I) as defined in claim 1 or a pharmaceutically acceptable salt thereof.

* * * * *